United States Patent [19]

Denance

[11] Patent Number: 5,034,003
[45] Date of Patent: Jul. 23, 1991

[54] INJECTION DEVICE HAVING A STABILIZING SIGHT WHICH ACTUATES A SAFETY VALVE FOR THE NEEDLE

[76] Inventor: Raymond Denance, Le commodore H41, Marina Baie des Anges, 06270 Villeneuve Loubet, France

[21] Appl. No.: 437,805

[22] Filed: Nov. 17, 1989

[30] Foreign Application Priority Data

Nov. 21, 1988 [FR] France ................ 88 15538

[51] Int. Cl.⁵ .............................................. A61M 5/00
[52] U.S. Cl. .................................. 604/117; 604/155; 604/131
[58] Field of Search ........ 604/117, 131, 134, 154–157, 604/192, 207–208, 211, 223, 224; 222/390, 391

[56] References Cited

U.S. PATENT DOCUMENTS

| | | | |
|---|---|---|---|
| 3,538,916 | 11/1970 | Wiles | 604/117 |
| 3,790,048 | 2/1974 | Luciano et al. | 604/211 |
| 4,067,334 | 1/1978 | Haller | 604/223 |
| 4,198,975 | 4/1980 | Haller | 604/157 |
| 4,333,459 | 6/1982 | Becker | 604/117 |

FOREIGN PATENT DOCUMENTS 2390175 12/1978 France .
2524321 10/1983 France .
2567760 1/1986 France .

*Primary Examiner*—Stephen C. Pellegrino
*Assistant Examiner*—Michael Rafa
*Attorney, Agent, or Firm*—Young & Thompson

[57] ABSTRACT

An injection device comprising a support stock that supports a syringe having a plunger and a needle. The plunger is movable in an axial direction to force liquid from the syringe through the needle. A safety valve prevents flow of liquid from the syringe to the needle. A stabilizing sight is provided, for application against skin during an injection. The stabilizing sight is mounted on the device for movement relative to the device such that when the device is pressed against the skin the needle moves from a retracted position relative to the stabilizing sight to an advanced position relative to the stabilizing sight to penetrate the skin. The stabilizing sight is interconnected with the safety valve in such a way that when the needle is in that advanced position the safety valve is moved to an open position and when the needle is in that retracted position the safety valve is in a closed position.

6 Claims, 5 Drawing Sheets

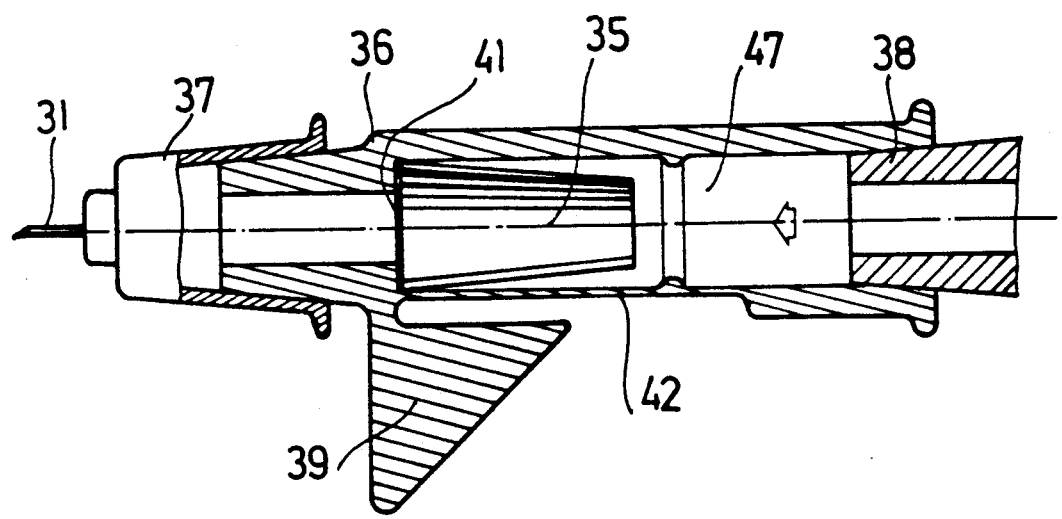
Fig_2
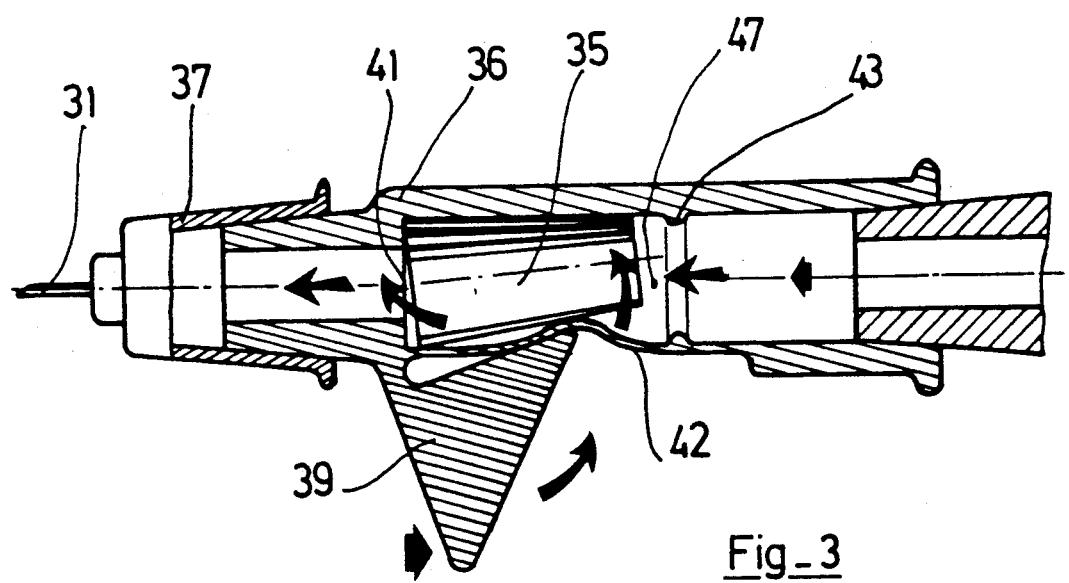
Fig_3

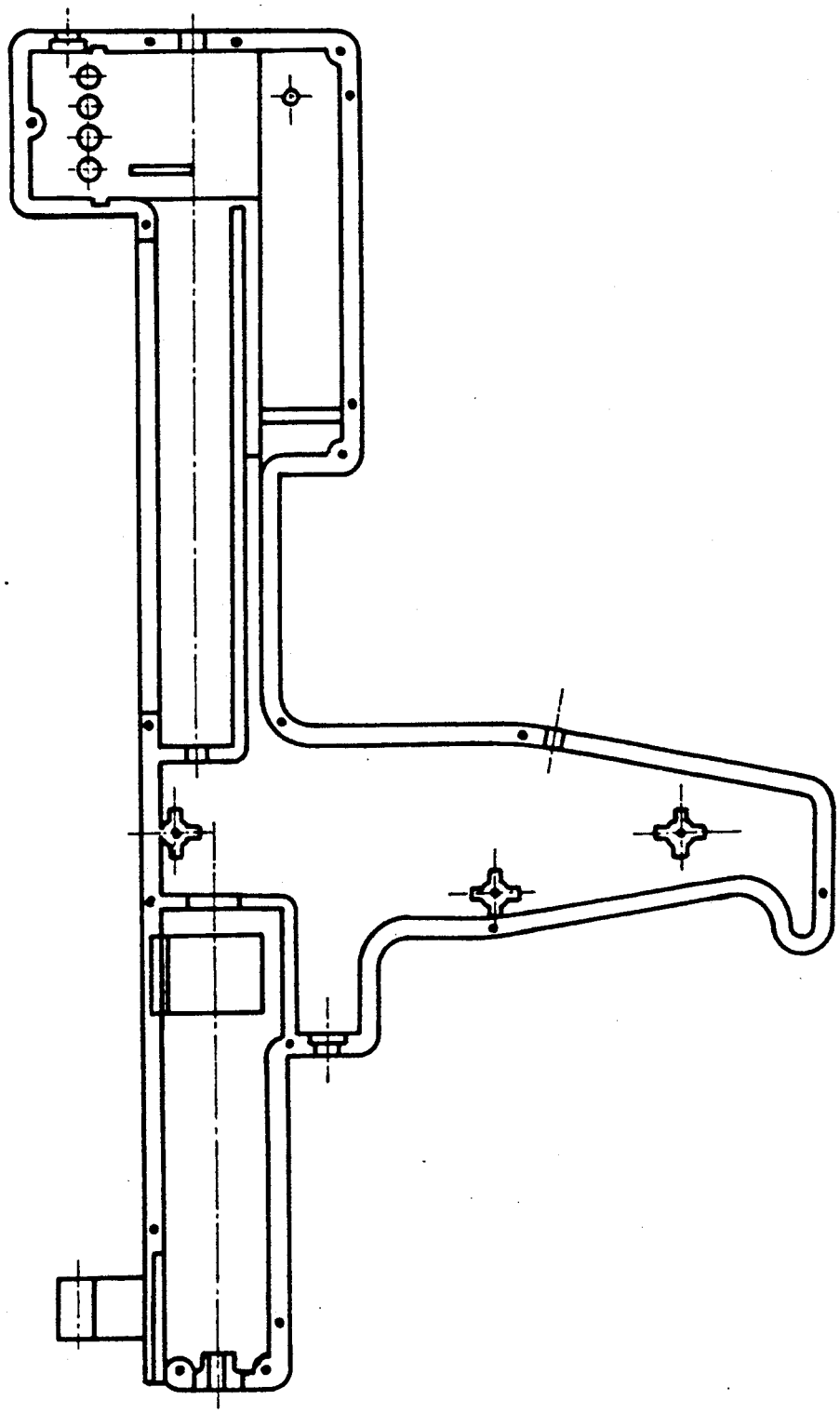

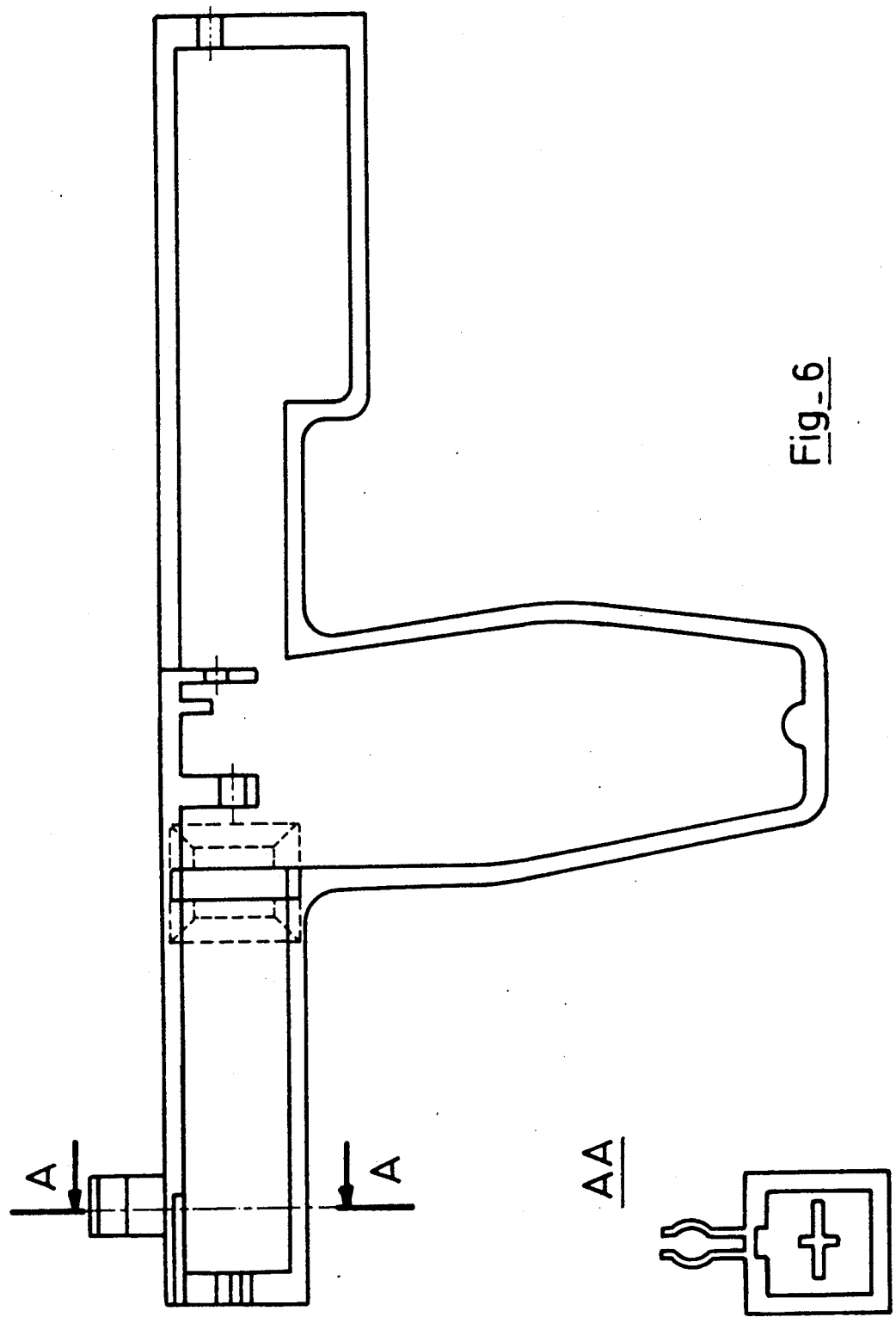
Fig_6
Fig_7

INJECTION DEVICE HAVING A STABILIZING SIGHT WHICH ACTUATES A SAFETY VALVE FOR THE NEEDLE

FIELD OF THE INVENTION

The invention comprises an injection device for medical and veterinary use, having a single-use stabilizing sight which actuates a means serving as a safety valve at the level of the needle.

This apparatus is intended to perform intradermic, subcutaneous or intramuscular injections for medical or veterinary use, and more particularly in mesotherapy, hydropuncture, vaccinations or allergological tests.

1. The Known Prior Art

The state of the art may be defined by French patent 2,524,321, of the same author. This patent describes a "manual or mechanical" injection device for medical and veterinary use. This patent describes an injection device which comprises: a support stock having the form of a revolver, a removable injection syringe provided with a syringe piston, a single injection needle or a multi-injector bearing several injection needles, a syringe cradle integrating the syringe with the support stock, means for positioning the impact and predetermining the degree of penetration of the needle or needles, mechanical transmission means comprising a ratchet and a barrel transmitting the exerted thrust, to enable penetration of the needle or needles and injection of the liquid.

The state of the art may also be defined by a patent such as HALLER, U.S. Pat. No. 4,198,975 and LUCIANO, U.S. Pat. No. 3,790,048.

These patents describe in particular pistols for making punctures, one of which pistols is electric, namely that described in the LUCIANO patent, whereas the other is completely mechanical, namely that described in the HALLER patent. Another patent is capable of defining the state of the art, namely French patent FR.B2.2.390.175.

This patent FR.B2.2.390.175 describes a process for mesotherapy treatment and its injection device forming a micro-injector which is automatic as regards application.

2. Background of the Invention

Problems associated with rapidly-spreading contagious diseases require a revision of this type of pistol for medical and veterinary use. For medical use, this type of pistol is especially used in mesotherapy. It is important that all of the parts of the injection device which contact the patient to be treated be of the single-use type.

Another problem occurs as a practical matter with this type of injection device such as defined by the state of the art. The pressure exerted by the piston on the syringe creates a certain inertia due to overpressure, which implies that at each exit of the needle from the skin, there is a loss of liquid. Droplets spill out, which is disagreeable for the patient as well as for the person using the injection device. This leakage of liquid also represents, in the case where the injected liquid is relatively expensive, a significant loss of money.

Finally, in the case of specific treatment such as treatment of cellulite, the user of the device must actuate the trigger 4 to 600 times so that the said device injects the liquid. After several treatments, fatigue results from using the mechanical devices now on the market.

The invention tends to solve all of these problems.

SUMMARY OF THE INVENTION

The device according to the invention is an injection device of the electric type comprising a support stock, a syringe received on the upper horizontal surface of the support stock and maintained forwardly by its tip which rests on a stirrup and rearwardly by the head of the piston of the syringe which is housed in a movable slide actuated by an electric motor which transmits the thrust for enabling penetration of the needle and injection of the liquid, a stabilizing sight of the skin guides and predetermines the degree of penetration of the needle by an adjustment.

The stabilizing sight is of the removable type, a means serving as a spring assures its maintenance in a hollow micrometer screw itself housed in a movable cylinder; the said movable cylinder comprising a movable finger which acts on a means serving as a safety valve disposed at the level of the injection needle.

The head of the piston for the syringe is in contact with the head of a piston situated in the movable slide, the piston is provided with a spring mounted coaxially with the rod of the piston; the said spring is housed in the movable slide, the cursor and piston assembly is actuated by the electric motor which acts on a threaded shaft on which is mounted the body of the slide which forms, at this level, a manipulating screw.

The head of the piston is in meshing engagement with the manipulating screw via a threaded shaft whose end rests on a bearing situated in the support stock and whose other end terminates in a toothed pinion which meshes with a toothed pinion situated at the output of a reducer disposed in extension of the electric motor.

In the electric and electronic embodiment, the motor may be a stepping motor; the motor meshes, via its shaft and its toothed wheel, with another wheel directly geared to the threaded shaft; on the threaded shaft is mounted a slide which is geared with the head of the piston of the syringe.

An operating commutator is disposed in extension of the shaft of the chamber and of the cylinder which houses the stabilizing site, this operating commutator assures the enabling of the automatic operation, continuous or simultaneous, through the action of the sight which latter is in contact with the skin;

forward progress contact;
rearward progress contact;
forward interrupter;
rear interrupter;
start/stop contact.

The device is provided with a signal, which is a sound signal, which is emitted at each injection.

The stabilizing sight extends via its end into an orifice of the anterior portion of the support stock; this end is housed in a hollow micrometer screw; the said hollow micrometer screw is threaded on its exterior face so as to be able to be displaced in a chamber of a movable cylinder provided to this end; the said movable cylinder is terminated by a shaft; the said shaft penetrates in a bearing, fixed to the support stock; a return spring is disposed coaxially to the said shaft between the chamber and the end of its shaft; an adjusting knob permits the shaft and the chamber to return; the said chamber of the movable cylinder comprises a screw threading in its interior body; the screw threading corresponds to the threading on the exterior face of the micrometer screw; by turning the adjusting knob, the axis of the chamber turns whereas the micrometer screw is displaced in the said chamber of the movable cylinder; this adjusting knob thus permits adjusting the depth of entry of the end of the sight and thus regulates the degree of penetration of the needle into the skin.

The stabilizing sight is terminated by its end which is cruciform and which penetrates in the body of the cylinder which is slit along its longitudinal axis and solely in its anterior portion, whereas a retaining means is positioned about the body of the cylinder to serve as a fixing spring.

The retaining means is a retaining ring which is positioned around the body of the hollow micrometer screw.

The device is provided with a means acting as a safety valve, disposed at the level of the injection needle, the said safety valve being associated with a means acting as a detector of penetration of the needle into the skin.

The body of the mounting for the safety valve is disposed between the fixation end of the needle and the end of the syringe where the needle is conventionally encased.

The body of the mounting for the safety valve is provided with a means acting as a lever, which is actuated by a movable finger; the said movable finger is screwed on the anterior end of the chamber of the movable cylinder; the hollow micrometer screw may also be threaded at this level and comprise a stopping abutment; the movable finger is exterior whereas its body is cylindrical so as to fit between the chamber of the movable cylinder and the micrometer screw; the said body of the mounting for the safety valve is thus controlled by a means which acts as a detector of penetration of the needle into the skin; when the needle is withdrawn from the skin, the safety valve closes the opening of the body of the mounting for the safety valve which closes the passage of liquid from the syringe to the needle through the said opening.

The means acting as a detector of penetration of the needle into the skin is a lever, the said lever acts at the level of the wall of the body of the mounting for the safety valve; the said wall is, at this level, slightly thinner; the said lever thus acts directly on the safety valve which is freely mounted in the chamber, which allows a tilting which disengages the said safety valve from the opening, which permits circulation of liquid between the syringe and the needle.

The chamber of the body of the mounting for the safety valve may comprise pins which permit force-fitting the safety valve in the said chamber, but prevent this latter from exiting therefrom.

The safety valve has a frusto-conical shape.

BRIEF DESCRIPTION OF THE DRAWINGS

The attached drawings are given by way of explanatory and non-limiting example. They show a preferred embodiment according to the invention. They will permit ready understanding of the invention.

FIG. 2 is a sectional view of the body of the mounting for the safety valve in closed position.

FIG. 3 is a sectional view showing the body of the mounting for the safety valve, its movable safety valve and the action of the lever which acts in the direction indicated by the arrows.

FIG. 5 is a schematic view of the injection device according to the invention, according to an electric or electronic embodiment.

FIG. 6 is a schematic view of the device according to the invention, according to another embodiment.

FIG. 7 is a sectional view along the line A—A of FIG. 6, of the support stock of the device showing the stirrup and the cruciform opening for the end of the stabilizing sight. In this embodiment the assembly is of single piece construction, formed by injection.

DETAILED DESCRIPTION OF THE INVENTION

Figures 1, 1A:
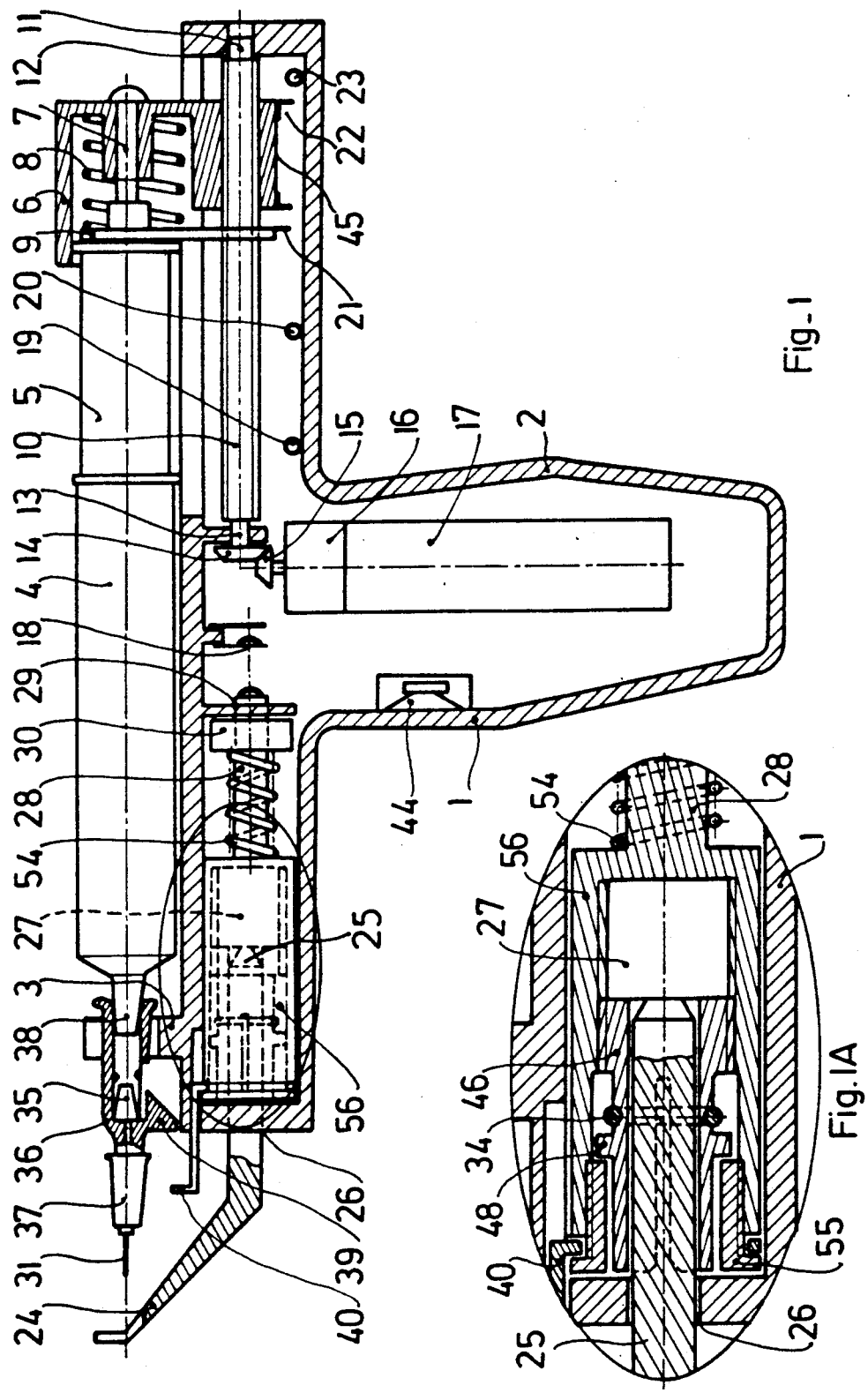
FIG. 1 is a sectional view of the injection device for medical and veterinary use, which displays the principal active members of the said device.
FIG. 1A is an enlarged fragment of FIG. 1, showing the means for securing the sight in the pistol.

The device according to the invention is an electric injection pistol. It comprises a support stock 1 having the form of a revolver. In its upper portion, and perpendicular to the handle 2 of the support stock 1, is disposed forwardly a stirrup 3 and rearwardly a movable slide 6. The syringe 4 is maintained at the level of its tip by the stirrup 3 on which the said tip rests and rearwardly by its piston 5 which is housed in a slide 6. The piston 5 of the syringe 4 is actuated by a piston 7 housed in the slide 6 whose rod is provided coaxially with a spring 8. The body of the slide 6 forms a manipulating screw 45, the said manipulating screw 45 of the movable slide 6 is in mesh with a threaded shaft 10 having an extremity 11 received in a bearing 12 situated in the support stock 1, and whose other extremity 13 terminates in a toothed pinion 14 which meshes with another toothed pinion 15 situated at the output of a reducer disposed in extension of the electric motor 17.

According to a preferred embodiment, the motor 17 and the reducer 16 are disposed in the handle 2 of the support stock 1.

The various operating contacts and commutators are as follows:

an operating commutator 18 is disposed in extension of the axis of the movable cylinder which houses the stabilizing sight, this operating commutator 18 assures the enabling of the automatic, continuous or simultaneous function, by action of the sight when this latter is in contact with the skin (this operating commutator may be a simple mechanical contact, or for example an optical detector);

19 is the forward progress contact;

20 is the rearward progress contact;

21, disposed in extension of the head 9 of the piston 7, is the forward interrupter;

22, integrated with the slide 6, is the rearward interrupter;

23 is the start/stop contact.

The device may be provided with a signal 44, which may be a sound signal or light signal.

In the embodiment shown, the said signal is a sound signal, as it may be interesting for the user to know the number of injections effected. Certain devices comprise counters which are difficult to read while manipulating the injection device. Other devices comprise display screens with light-emitting diodes which have the same disadvantage as a numerical counter.

The audible or luminous signal according to the invention has the advantage of familiarizing the practitioner with a rhythm, for example sound, which corresponds to a quantity of liquid in cubic millimeters, injected into the patient.

Without counting in a precise manner the number of injections, by the simple cadence and the elapsed time, the user knows that he has injected the necessary and sufficient quantity of liquid. The body of the slide 6 is extended beyond the axis of the syringe 4 so as to serve as a manipulating screw 45 with the threaded shaft 10.

As indicated in the preface of the invention, the stabilizing sight 24 is of the single-use type, which thus prevents problems due to contagious diseases.

The stabilizing sight 24 penetrates via its extremity 25 into an opening 26 of the anterior part of the support stock 1. This extremity 25 is housed in a hollow micrometer screw 46 whose exterior parts are threaded (see FIG. 1). The said micrometer screw 46 is threaded on its exterior surface so as to be able to be displaced in the chamber 27 of a movable cylinder 56 provided to this end. The said chamber 27 of the movable cylinder 56 is terminated by a shaft 28. The said shaft 28 is received in a bearing 29, integrated with the support stock. A return spring 54 is disposed coaxially with the said shaft 28 between the chamber 27 of the movable cylinder 56 and the end of its shaft 28. An adjusting knob 30 permits turning the shaft 28 and the chamber 27 of the movable cylinder 56. The said chamber 27 of the movable cylinder 56 comprises a screw threading in its interior body. The screw threading corresponds to the threading of the micrometer screw 46. By causing the adjusting knob 30 to turn, the shaft 28 and the chamber 27 of the movable cylinder 56 turn whereas the micrometer screw 46 is displaced in the said chamber 27 of the movable cylinder 56. This adjusting knob 30 thus permits adjusting the depth of entry of the extremity 25 of the sight 24 and thus adjusting the degree of penetration of the needle 31 in the skin. The said knob 30 thus adjusts the course of the stabilizing sight 24 and for guiding thus serves at the same time as a means for adjusting the penetration of the needle 31 in the skin. The assembly of the movable cylinder 56 and hollow micrometer screw 46 is maintained in the body of the support stock by a hollow threaded bolt 55 which permits the extremity 25 to extend from the stabilizing sight 24.

The stabilizing sight 24 is terminated at its extremity 25 which is cruciform and which penetrates into the cylindrical body 46 which is slit along its longitudinal axis and solely in its anterior portion whereas a retaining means 34 is positioned so as to assure the fixation of this extremity 25.

According to the embodiment of FIG. 1, the retaining means is a retaining ring 34 which is positioned around the body of the hollow micrometer screw 46.

The stabilizing sight 24 is thus removable, and may be securely received in or removed from its housing; it is thus adapted for a single use, and is disposable.

One of the characteristics of the invention resides in the fact that the injection device is provided with a means 35 acting as a safety valve disposed at the level of the injection needle 4.

This device acting as a safety valve prevents the problems of leakage of the injection fluid.

A mounting body for the safety valve 36 is disposed between the fixation cap 37 of the needle and the cap 38 of the syringe where the needle would conventionally be received.

The said mounting body for the safety valve 36 is provided with a means acting as a lever 39 which is actuated by a movable finger 40. The said movable finger 40 is screwed on the anterior end of the chamber 27 of the movable cylinder 56. To this end, the micrometer screw 46 may also be threaded at this level and comprise a stopping abutment 48. The movable finger 40 is exterior, whereas its body is cylindrical so as to be received between the chamber 27 of the movable cylinder 56 and the micrometer screw 46.

The said mounting body for the safety valve 36 is thus controlled by a means acting as a penetration detector for the needle 31 into the skin. When the needle 31 is withdrawn from the skin, the safety valve 35 closes the opening of the body of the mounting for the valve 36, which blocks the passage of liquid from the syringe 4 toward the needle 31 through the said opening.

The means acting as lever 39 is a detector of penetration of the needle into the skin. The said lever 39 acts directly on the wall 42 of the body of the mounting for the safety valve 36. The said wall 42 is, at this level, slightly thinner. The said lever 39 thus acts directly on the safety valve 35. The safety valve 35 is disengaged from the opening 41 which permits circulation of liquid between the syringe 4 and the needle 31. The constitution of the body of the mounting for the safety valve 36 may be of plastic whose performance characteristics are especially those known as "memory plastic" which resumes its shape after actuation of the lever 39 on the flexible wall 42, such that the said lever 39 may deform the said wall and act interiorly of the chamber 47 on the valve 35. The chamber 47 of the body of the mounting for safety valve 36 may comprise pins 43 which permit force-fitting the valve 35 in the said chamber 47, but prevent this latter from exiting therefrom. The said valve 35 is thus freely mounted in the chamber 47.

So as to be able to generate and regulate the injection pressure, the rod of the piston is terminated exteriorly of the piston by a threaded orifice 54 in which is received a screw 55 whose head is exterior to the slide 6. Action on the screw 55 permits adjusting the pressure of the spring 8 which is housed in the chamber of the slide 6. Adjustment of the tension of the spring 8 permits adjusting the injection pressure or power.

According to a preferred embodiment, the valve 35 has a frusto-conical shape, whose top is directed toward the syringe 4 and whose base closes the opening 41 of the chamber 47. The valve 35 may have a frusto-conical shape which facilitates the rocking and disengagement from the orifice 41 under the action of the lever 39.

Figure 4:
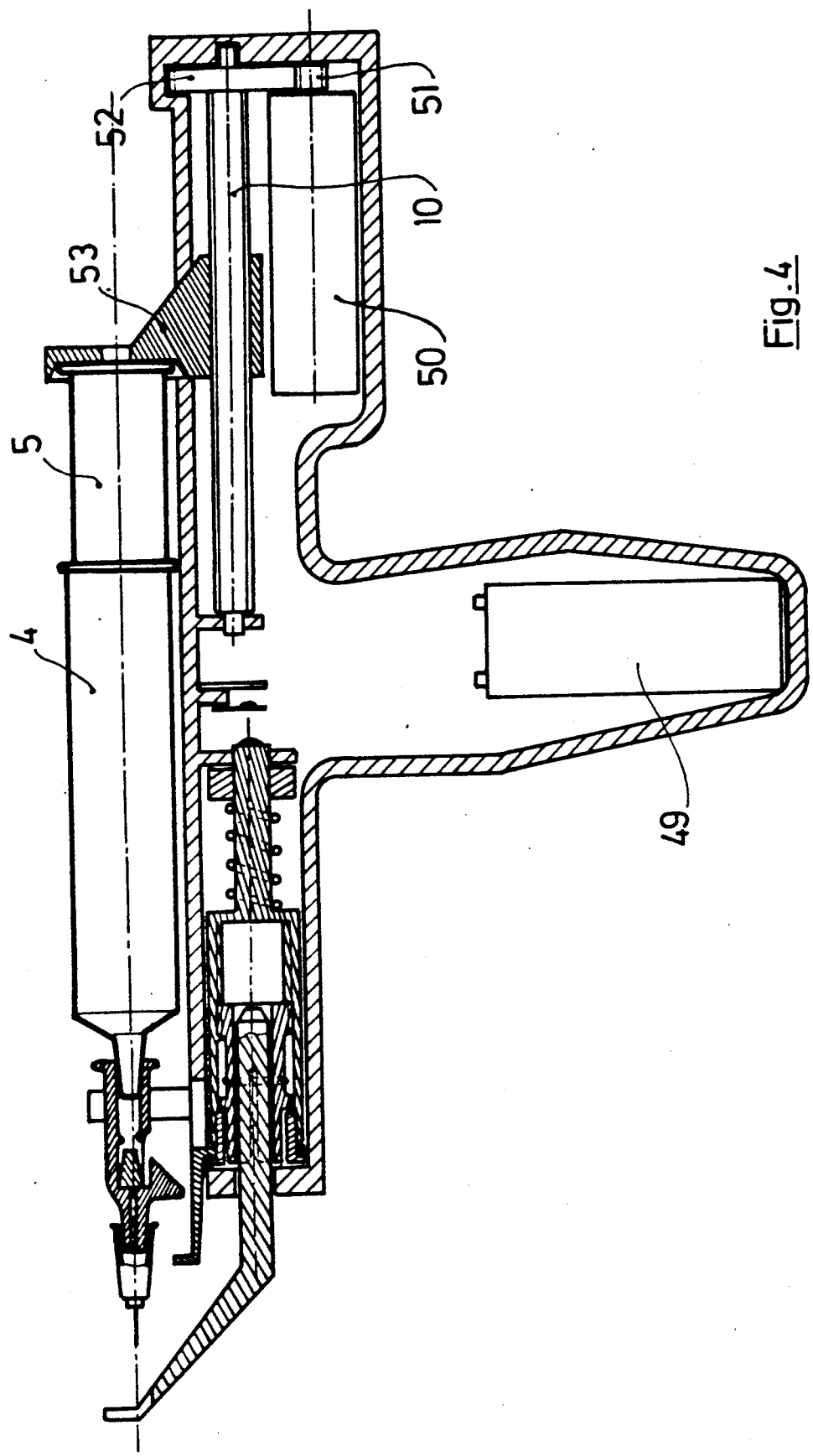
FIG. 4 is a sectional view of the injection device adapted for electric energization by rechargeable or non-rechargeable batteries or cells.

FIG. 4 shows another electric and electronic embodiment, which permits a choice of programs for injection as a function of the diseases to be treated and of the choice of the apparatus based on the medicine. The motor 50 may in this case be a stepping motor and the power mechanism at the level of the piston of the syringe may be different. In the case shown in FIG. 4, the motor 50 meshes via its shaft and its toothed wheel 51, with another wheel 52 directly geared with the threaded shaft 10. On the threaded shaft 10 is mounted a slide 53 which engages with the head of the piston 5 of the syringe 4.

REFERENCES 1. Support stock 2. Handle 3. Stirrup 4. Syringe 5. Piston 6. Movable slide 7. Piston 8. Return spring 9. Piston head 10. Threaded shaft 11. Extremity of the shaft 12. Bearing 13. Extremity of the shaft 14. Toothed pinion 15. Toothed pinion 16. Reducer 17. Electric motor 18. Operating commutator 19. Forward travel contact 20. Rearward travel contact 21. Forward interrupter 22. Rear interrupter 23. Start/stop contact 24. Stabilizing sight 25. Extremity of the stabilizing sight 26. Orifice 27. Chamber of the movable cylinder 28. Shaft 29. Bearing 30. Knob 31. Needle 34. Retaining ring 35. Valve 36. Body of the support for the valve 37. Fixation cap for the needle 38. Cap for the syringe 39. Lever 40. Movable finger 41. Orifice 42. Flexible wall 43. Pins 44. Sound signal 45. Manipulating screw 46. Hollow micrometer screw receiving the extremity 25 of the stabilizing sight 24 47. Chamber of the body of the safety valve 48. Stoppage abutment situated on the exterior face of the micrometer screw 49. Cells or batteries 50. Electric stepping motor 51. Toothed wheel of the second embodiment 52. Wheel of the second embodiment 53. Slide of the second embodiment 54. Return spring 55. Hollow threaded bolt 56. Movable cylinder

I claim:

1. An injection device comprising a support stock that supports a syringe having a plunger and a needle, means to move the plunger in an axial direction to force liquid from the syringe through the needle, a safety valve for preventing flow of liquid from the syringe to the needle, a stabilizing sight for application against skin during an injection, means mounting the stabilizing sight on the device for movement relative to the device such that when the device is pressed against the skin the needle moves from a retracted position relative to the stabilizing sight to an advanced position relative to the stabilizing sight to penetrate the skin, and means interconnecting the stabilizing sight and the safety valve such that when the needle is in said advanced position the safety valve is in an open position and when the needle is in said retracted position the safety valve is in a closed position.

2. A device as claimed in claim 1, further comprising means yieldably resiliently urging said sight toward a forward position in which said needle is in said retracted position.

3. A device as claimed in claim 1, wherein said safety valve is disposed in a resiliently deformable conduit between said syringe and said needle, said interconnecting means comprising means movable with said stabilizing sight to deform said deformable conduit thereby to open said safety valve.

4. A device as claimed in claim 3, wherein said interconnecting means comprises a finger that swings a resilient portion of said device to deform said deformable conduit.

5. A device as claimed in claim 1, further including an electric motor having an output shaft, means drivingly interconnecting said output shaft with said plunger to move said plunger in said axial direction, and switch means carried by the device for actuating said electric motor to move the plunger.

6. A device as claimed in claim 5, wherein said means interconnecting said output shaft and said plunger comprises a threaded shaft rotatable by said output shaft, and screw threaded means movable along said threaded shaft upon rotation of said threaded shaft to move said plunger in said axial direction.

* * * * *